US008815958B2

(12) United States Patent
Sasaki et al.

(10) Patent No.: US 8,815,958 B2
(45) Date of Patent: Aug. 26, 2014

(54) WATER-IN-OIL TYPE EMULSION SKIN COSMETIC

(75) Inventors: Kazutaka Sasaki, Yokohama (JP); Takayuki Omura, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/497,640

(22) PCT Filed: Sep. 22, 2010

(86) PCT No.: PCT/JP2010/066361
§ 371 (c)(1),
(2), (4) Date: Apr. 23, 2012

(87) PCT Pub. No.: WO2011/037123
PCT Pub. Date: Mar. 31, 2011

(65) Prior Publication Data
US 2012/0220670 A1  Aug. 30, 2012

(30) Foreign Application Priority Data
Sep. 25, 2009 (JP) ................................. 2009-221121

(51) Int. Cl.
*B01F 3/08* (2006.01)

(52) U.S. Cl.
USPC .................. 516/21; 424/401; 516/23; 516/34

(58) Field of Classification Search
USPC .................................. 424/401; 516/21, 23, 34
See application file for complete search history.

(56) References Cited

U.S. PATENT DOCUMENTS

| | | | |
|---|---|---|---|
| 5,612,044 A * | 3/1997 | Suares et al. .................. 424/401 |
| 2001/0012860 A1* | 8/2001 | Bleckmann et al. ............ 516/21 |
| 2004/0137025 A1 | 7/2004 | Kosugi et al. |
| 2005/0191328 A1* | 9/2005 | Taniguchi ...................... 424/401 |
| 2006/0088562 A1* | 4/2006 | Brieva et al. .................. 424/401 |
| 2007/0264292 A1* | 11/2007 | Kurosawa et al. ............. 424/401 |

FOREIGN PATENT DOCUMENTS

| | | |
|---|---|---|
| EP | 1 374 835 | 1/2004 |
| EP | 2 014 701 | 1/2009 |
| JP | 11-246348 | 9/1999 |
| JP | 2000159629 | 6/2000 |
| JP | 2000159629 A * | 6/2000 |
| JP | 2001131421 | 5/2001 |
| JP | 2001199846 | 7/2001 |
| JP | 2004026833 | 1/2004 |
| JP | 2005232068 | 9/2005 |
| JP | 2007230923 | 9/2007 |
| JP | 2008115358 | 5/2008 |
| JP | 2008297206 | 12/2008 |
| JP | 2009143834 | 7/2009 |
| JP | 2011068598 | 4/2011 |

OTHER PUBLICATIONS

PCT/JP2010/066361 Search Report mailed Dec. 28, 2010, 2 pages—Japanese; 2 pages-English.
JP 2009-221121—Decision to Grant a Patent mailed Jul. 6, 2012, 3 pages—English; 3 pages-Japanese.
JP 2009-221121—Appeal Brief/Amendment dated Apr. 26, 2012, 7 pages—English; 6 pages-Japanese.
JP 2009-221121—Written Arguments dated Feb. 15, 2011, 4 pages—English, 3 pages-Japanese.
JP 2009-221121—Written Amendments (spec) dated Feb. 15, 2011; 1 page-English, 1 page-Japanese.
JP 2009-221121—Notice of Reasons for Rejection dated Dec. 21, 2010, 3 pages—English, 3 pages-Japanese.
JP 2009-221121—Notice of Appeal/Request for an Appeal dated Mar. 16, 2012, 1 pages—English, 1 page-Japanese.
JP 2009-221121—Written Amendment(s) dated Mar. 16, 2011; 1 page—English, 1 page-Japanese.
JP 2009-221121—Decision of Rejection mailed Dec. 16, 2011, 3 pages—English, 3 pages-Japanese.

* cited by examiner

*Primary Examiner* — Ali Soroush
(74) *Attorney, Agent, or Firm* — Andrew F. Young, Esq.; Lackenbach Siegel, LLP

(57) ABSTRACT

A skin cosmetic in which the emulsion stability can be ensured by adding a volatile hydrocarbon oil to a water-in-oil-type emulsion composition containing a non-volatile silicone oil, and which has an excellent non-oily sensation upon application. Specifically disclosed is a water-in-oil-type emulsion skin cosmetic which is characterized by comprising (A) 3 to 25% mass of a volatile hydrocarbon oil, (B) 0.1 to 15% by mass of a non-volatile silicone oil, (C) 0.1 to 1% by mass of a polyethylene glycol mono- or di-isostearate having 4 to 12 oxyethylene groups, (D) 0.1 to 5% by mass of a polyoxyethylene-polydimethylsiloxyethyl-dimethicone copolymer, and (E) an organically-modified clay mineral.

7 Claims, No Drawings

WATER-IN-OIL TYPE EMULSION SKIN COSMETIC

CROSS REFERENCE TO RELATED APPLICATIONS

This application relates to and claims priority from PCT/JP2010/066361 filed Sep. 22, 2010, the entire contents of which are incorporated herein by reference, which in turn claims priority from JP 2009-221121 filed Sep. 25, 2009.

BACKGROUND OF THE INVENTION

1. Field of the Invention

The present invention relates to a water-in-oil-type emulsion skin cosmetic that is excellent in stability and has non-oily usability. More specifically, the present invention relates to a water-in-oil-type emulsion skin cosmetic comprising a volatile hydrocarbon oil and a non-volatile silicone oil, which is excellent in emulsification stability.

2. Description of the Related Art

Water-in-oil-type skin cosmetics have been used as skin cosmetics for use in applications, such as sunscreen cosmetics, for which water resistance is required. However, since water-in-oil-type emulsions inevitably contain relatively a large amount of oil component, they have a problem in usability that it is felt oily when they are applied to the skin.

In order to improve the oily feeling of water-in-oil-type emulsions, a volatile oil component is incorporated. However, in some emulsions mainly comprising a volatile silicone oil as a volatile oil component, surface-slip feeling and squeaky feeling become strong and suitable moist feeling is lost after application. On the other hand, there has been a problem that, when a volatile hydrocarbon oil component is incorporated into a water-in-oil-type emulsion comprising a non-volatile silicone oil, surface-slip feeling and squeaky feeling are improved, but the stability of the emulsion over time is decreased.

Patent Document 1 describes a cosmetic composition having transfer resistance, comprising a non-volatile silicone compound and a non-volatile hydrocarbon oil component that is non-compatible with the silicone. This cosmetic comprises a volatile hydrocarbon oil component (solvent) in which a non-volatile hydrocarbon oil can be dissolved and a non-volatile silicone compound can be dissolved or dispersed, and has improved transfer resistance by specifying the solution parameter of the above-mentioned non-volatile hydrocarbon oil component.

Patent Document 2 describes a water-in-oil-type emulsion composition comprising fibers, a silicone surfactant and a clay, which is considered to have fine stability even at a high temperature (such as 45° C.).

Furthermore, Patent Document 3 describes a water-in-oil-type emulsified sunscreen cosmetic comprising a zinc oxide powder that has been subjected to a special surface-hydrophobization treatment, a volatile silicone, a polyoxyalkylene-modified organopolysiloxane and water. The literature describes that this water-in-oil-type emulsion cosmetic may further comprise an organically-modified clay mineral, and an emulsion in which the above-mentioned powder had been incorporated stably without increasing the amount of the oil component such as a non-volatile silicone was obtained.

However, the problem that the stability of a water-in-oil-type emulsion comprising a non-volatile silicone is deteriorated when a volatile hydrocarbon oil component is incorporated into the emulsion has not been recognized at all in prior arts including Patent Documents 1 to 3, and thus any solution for such problem has not been disclosed or suggested.

PRIOR ART DOCUMENTS

Patent Documents

Patent Document 1: JP-A No. 2001-199846
Patent Document 2: JP-A No. 2001-131421
Patent Document 3: JP-A No. 2005-232068

ASPECTS AND SUMMARY OF THE INVENTION

Problem to be Solved by the Invention

Therefore, the problem in the present invention is to provide a skin cosmetic that can ensure emulsification stability and has excellent usability such as non-oiliness, even in the case when a non-volatile hydrocarbon oil is added to a water-in-oil-type emulsion composition comprising a non-volatile silicone oil.

The present inventors have done intensive studies aiming at solving the above-mentioned problem, and consequently found that it is necessary to form a stable oil gel in order to obtain a stable water-in-oil-type emulsion cosmetic comprising a volatile hydrocarbon oil and a non-volatile silicone oil, and that the above-mentioned problem can be solved and a stable skin cosmetic that is excellent in usability can be obtained by incorporating a polyethylene glycol mono- or di-isostearate having a predetermined number of oxyethylene groups, a polyoxyethylene-polymethylsiloxyethyl dimethicone and an organically-modified clay mineral in combination, and completed the present invention.

Solution to Problem

Namely, the present invention provides a water-in-oil-type emulsion skin cosmetic comprising:
(A) 3 to 40% by mass of a volatile hydrocarbon oil,
(B) 0.1 to 25% by mass of a non-volatile silicone oil,
(C) 0.1 to 1% by mass of a polyethylene glycol mono- or di-isostearate comprising 4 to 12 oxyethylene groups,
(D) 0.1 to 5% by mass of a polyoxyethylene-polydimethylsiloxyethyl-dimethicone copolymer, and
(E) 0.1 to 3% by mass of an organically-modified clay mineral.

Effects of the Invention

Since the skin cosmetic of the present invention comprises a volatile hydrocarbon oil, it has no oily feeling, or has no surface-slip feeling or squeaky feeling, but is excellent in usability, and can impart moist feeling to the skin after application. Furthermore, it is also excellent in the stability of the emulsion over time.

MODES FOR CARRYING OUT THE INVENTION

The skin cosmetic of the present invention comprises a volatile hydrocarbon oil (component A). The volatile hydrocarbon oil used in the present invention is not specifically limited as long as it is a hydrocarbon oil having volatility at an ordinary temperature which has conventionally been used for cosmetics and the like, and examples may include isododecane, isohexadecane, hydrogenated polyisobutene and the like.

The incorporation amount of the volatile hydrocarbon oil in the cosmetic of the present invention is 3 to 40% by mass, preferably 3 to 30% by mass, more preferably 3 to 25% by mass. When the incorporation amount is less than 3% by mass, an improvement of oily feeling during use becomes insufficient, and when the component is incorporated by more than 40% by mass, the stability of the emulsion is decreased.

The cosmetic of the present invention comprises a non-volatile silicone oil (component B). Although those used as the non-volatile silicone oil are not specifically limited, examples may include methylpolysiloxane 6 cs, methylpolysiloxane 20 cs, methylpolysiloxane 100 cs, methylphenylpolysiloxane, amino-modified silicone, fluorine-modified dimethylpolysiloxane and the like.

The incorporation amount of the non-volatile silicone oil in the cosmetic of the present invention is 0.1 to 25% by mass, preferably 0.1 to 20% by mass, more preferably 0.1 to 15% by mass. When the incorporation amount is less than 0.1% by mass, it is not possible to feel the smoothness of the skin after application, and when the non-volatile silicone oil is incorporated by more than 25% by mass, surface-slipping becomes strong and sufficient usability cannot be obtained.

The cosmetic of the present invention comprises a polyethylene glycol mono- or di-isostearate (component C), and this polyethylene glycol mono- or di-isostearate needs to have 4 to 12 oxyethylene groups. In some cases when the number of the oxyethylene groups is 3 or less, the desired effect may not be obtained. Specifically, commercial products such as PEG (4) diisostearate (EMALEXDEG-di-IS: Nihon Emulsion Co., Ltd.), PEG (8) diisostearate (EMALEX400di-ISEX: Nihon Emulsion Co., Ltd.) and PEG (10) monoisostearate (EMALEXPIE-10ES: Nihon Emulsion Co., Ltd.) can be used.

The incorporation amount of the polyethylene glycol mono- or di-isostearate (component C) in the cosmetic of the present invention is 0.1 to 1% by mass, preferably 0.1 to 0.8% by mass. When the incorporation amount is less than 0.1% by mass, the stability of the formulation over time is deteriorated, and when the component is incorporated by more than 1% by mass, the emulsification property is deteriorated and thus a formulation cannot be obtained.

The cosmetic of the present invention comprises a polyoxyethylene-polydimethylsiloxyethyl-dimethicone copolymer (component D). This encompasses, for example, those described as polyoxyalkylene-modified organopolysiloxanes in the above-mentioned Patent Document 3. Such polyoxyethylene-polydimethylsiloxyethyl-dimethicone copolymer is also disclosed in, for example, JP-A No. 2002-179548, and Silicone KF-6028 that is a commercial product (manufactured by Shin-Etsu Chemical Co., Ltd.) can also be used. This has a labeling name of PEG-9 polydimethylsiloxyethyl dimethicone.

The incorporation amount of the polyoxyethylene-polydimethylsiloxyethyl-dimethicone copolymer (component D) in the cosmetic of the present invention is 0.1 to 5% by mass, preferably 0.1 to 3% by mass. When the incorporation amount is less than 0.1% by mass, excellent emulsification stability is difficult to be obtained, and when the component is incorporated by more than 5% by mass, the stability of the formulation over time is deteriorated.

The organically-modified clay mineral (component E) to be incorporated in the cosmetic of the present invention is one used as an emulsification aid, and it is preferable to use a kind of colloidal hydrous aluminum silicate having a three-layer structure, which is generally obtained by modifying a clay mineral represented by the following formula with a quaternary ammonium salt-type cation surfactant:

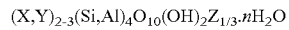

wherein X=Al, Fe (III), Mn (III) or Cr (III); Y=Mg, Fe (II), Ni, Zn or Li; Z=K, Na or Ca.

Specifically, it can be obtained by treating a clay mineral such as a montmorillonite group including natural montmorillonites such as montmorillonite, saponite and hectorite or synthetic montmorillonites (in this case, montmorillonites wherein the (OH) group in the formula has been replaced with fluorine) (commercial products include Begum, Kunipia, Laponite and the like) and synthetic micas that are known under the names of sodium silicic mica and sodium or lithium taeniolite (commercial products include Dimonite by Topy Industries Ltd., and the like) with a quaternary ammonium salt-type cation surfactant.

The quaternary ammonium salt-type cation surfactant as used herein is represented by the following formula.

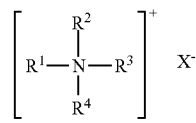

wherein $R^1$ represents an alkyl group or benzyl group having 10 to 22 carbon atoms, $R^2$ represents a methyl group or an alkyl group having 10 to 22 carbon atoms, $R^3$ and $R^4$ each represents an alkyl group or hydroxyalkyl group having 1 to 3 carbon atom(s), and X represents a halogen atom or a methyl sulfate residue.

Examples of such quaternary ammonium salt-type cationic surfactant may include dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylaminonium chloride, dibehenyldihydroxyethylammonium chloride and corresponding bromides, and the like, as well as dipalmitylpropylethylammonium methylsulfate, and the like. In carrying out the present invention, one kind or two or more kinds of these are optionally selected.

Typical examples of the organically-modified clay mineral may include dimethyldistearylammonium hectorite, benzyldimethylstearylammonium hectorite, distearyldimethylammonium chloride-treated aluminum magnesium silicate and the like. Examples of commercial products may include Benton 27 (benzyldimethylstearylammonium hectorite: manufactured by Elementis Specialties) and Benton 38 (distearyldimethylammonium chloride-treated hectorite: manufactured by Elementis Specialties).

The incorporation amount of the organically-modified clay mineral (component E) in the cosmetic of the present invention is 0.1 to 3% by mass, preferably 0.1 to 2.5% by mass. When the incorporation amount is less than 0.1% by mass, excellent emulsification stability is difficult to be obtained, and when incorporated by more than 3% by mass, the hardness of the formulation increases and thus sufficient usability cannot be obtained.

In the cosmetic of the present invention, in addition to the above-mentioned components A to E, other components that may be generally incorporated in skin cosmetics can be incorporated to the extent that the effect of the present invention is not inhibited. Specific examples of such components may include powders, oil-soluble ultraviolet absorbers, water-soluble ultraviolet absorbers, metal ion sequestering agents, neutralizing agents, adjusting agents, antioxidants, antibacterial agents, various drugs, various extracts and the like.

The skin cosmetic of the present invention can eliminate oily feeling and impart moist feeling by incorporating the volatile hydrocarbon. Therefore, it can be used as a skin cosmetic for use in applications for which water-in-oil-type emulsion cosmetics have conventionally been used.

EXAMPLES

Hereinafter the present invention will be explained in more detail with reference to specific examples below, but the present invention is not construed to be limited to the following Examples. Furthermore, unless otherwise stated, the incorporation amounts in the following Examples and the like represent % by mass.

The water-in-oil-type emulsion compositions of the present invention (Examples) and the compositions of Comparative Examples were prepared, and evaluated for the following respective items.

Oil Gel State

The composition was evaluated by the appearance after leaving the composition at room temperature for 1 week.

The case when the appearance was homogeneous: ○, the case when the appearance was not homogeneous: x Emulsification Property This was evaluated by observing the emulsion when the emulsion had emulsified.

The case when the emulsion emulsified homogeneously: ○, the case when the emulsion did not emulsified homogeneously: x Stability Over Time This was evaluated by the appearance of the emulsion as prepared after the emulsion was left at room temperature for 4 weeks.

Usability

Each of the samples as prepared was used by expert panelists (N=3), and the feeling of use immediately after the use was evaluated.

Samples having the compositions listed in the following Tables 1 and 2 were each prepared and evaluated for the above-mentioned respective items.

TABLE 1

|  | Comparative Example 1 | Comparative Example 2 | Comparative Example 3 | Comparative Example 4 | Comparative Example 5 | Comparative Example 6 |
| --- | --- | --- | --- | --- | --- | --- |
| Dimethyldistearylammonium hectorite | 2 | 2 | 2 | 2 | 2 | 2 |
| PEG-10 dimethicone | 2 | 2 | 2 | 2 | — | — |
| PEG-9 polydimethylsiloxyethyl dimethicone | — | — | — | — | 2 | — |
| Polyglyceryl diisostearate | — | — | — | — | — | — |
| Polyethylene glycol diisostearate (PEG8) | — | — | — | — | — | 2 |
| Liquid paraffin (non-volatile hydrocarbon oil) | 10 | — | — | 5 | 5 | 5 |
| Isohexadecane (volatile hydrocarbon oil) | — | 15 | — | 7 | 7 | 7 |
| Isododecane (volatile hydrocarbon oil) | — | — | 15 | 3 | 3 | 3 |
| Cyclomethicone (volatile silicone oil) | 5 | — | — | — | — | — |
| Methylpolysiloxane 6cs (non-volatile silicone oil) | 12 | 12 | 12 | 12 | 12 | 12 |
| Cetyl 2-ethylhexanoate | 5 | 5 | 5 | 5 | 5 | 5 |
| Trisodium edetate | 0.1 | 0.1 | 0.1 | 0.1 | 0.1 | 0.1 |
| Citric acid | 0.08 | 0.08 | 0.08 | 0.08 | 0.08 | 0.08 |
| Sodium citrate | 0.02 | 0.02 | 0.02 | 0.02 | 0.02 | 0.02 |
| Glycerin | 20 | 20 | 20 | 20 | 20 | 20 |
| Phenoxyethanol | 0.3 | 0.3 | 0.3 | 0.3 | 0.3 | 0.3 |
| Purified water | Balance | Balance | Balance | Balance | Balance | Balance |
| Oil gel state | ○ | X | X | X | X | X |
| Emulsification property | ○ | ○ | ○ | ○ | ○ | ○ |
| Stability over time 4 weeks | Fine | Separated | Separated | Separated | Separated | Separated |
| Usability | X(*) | — | — | — | — | — |

(*)Oily

TABLE 2

|  | Comparative Example 7 | Comparative Example 8 | Comparative Example 9 | Comparative Example 10 | Comparative Example 11 | Example 1 |
| --- | --- | --- | --- | --- | --- | --- |
| Dimethyldistearylammonium hectorite | 2 | 2 | 2 | 2 | 2 | 2 |
| PEG-10 dimethicone | — | 1.5 | 1.5 | 1.5 | — | — |
| PEG-9 polydimethylsiloxyethyl dimethicone | — | 0.5 | — | — | 1.5 | 1.5 |
| Polyglyceryl diisostearate | — | — | 0.5 | — | 0.5 | — |
| Polyethylene glycol diisostearate (PEG8) | 2 | — | — | 0.5 | — | 0.5 |
| Liquid paraffin (non-volatile hydrocarbon oil) | 5 | 5 | 5 | 5 | 5 | 5 |
| Isohexadecane (volatile hydrocarbon oil) | 7 | 7 | 7 | 7 | 7 | 7 |
| Isododecane (volatile hydrocarbon oil) | 3 | 3 | 3 | 3 | 3 | 3 |
| Cyclomethicone (volatile silicone oil) | — | — | — | — | — | — |

TABLE 2-continued

|  | Comparative Example 7 | Comparative Example 8 | Comparative Example 9 | Comparative Example 10 | Comparative Example 11 | Example 1 |
|---|---|---|---|---|---|---|
| Methylpolysiloxane 6cs (non-volatile hydrocarbon oil) | 12 | 12 | 12 | 12 | 12 | 12 |
| Cetyl 2-ethylhexanoate | 5 | 5 | 5 | 5 | 5 | 5 |
| Trisodium edetate | 0.1 | 0.1 | 0.1 | 0.1 | 0.1 | 0.1 |
| Citric acid | 0.08 | 0.08 | 0.08 | 0.08 | 0.08 | 0.08 |
| Sodium citrate | 0.02 | 0.02 | 0.02 | 0.02 | 0.02 | 0.02 |
| Glycerin | 20 | 20 | 20 | 20 | 20 | 20 |
| Phenoxyethanol | 0.3 | 0.3 | 0.3 | 0.3 | 0.3 | 0.3 |
| Purified water | Balance | Balance | Balance | Balance | Balance | Balance |
| Oil gel state | X | X | X | X | X | ○ |
| Emulsification property | X | ○ | ○ | ○ | ○ | ○ |
| Stability over time 4 weeks | Separated | Separated | Separated | Separated | Separated | Separated |
| Usability | — | — | — | — | — | Fine |

In Comparative Examples 2 and 3 that were obtained by replacing the volatile silicone oil of Comparative Example 1 in which a homogeneous oil gel was obtained with a volatile hydrocarbon, a homogeneous oil gel could not be obtained and the oil gel was separated. Furthermore, a stable oil gel could not be obtained and the oil gel was separated also in Comparative Examples 4 to 11, which lacked any of the polyethylene glycol mono- or di-isostearate (component C), polyoxyethylene-polymethylsiloxyethyl dimethicone copolymer (component D) and organically-modified clay mineral (component E). In addition, in Comparative Example 1 that contained a volatile silicone but did not contain a volatile hydrocarbon oil, a homogeneous emulsion could be obtained but the emulsion had oily feeling of use.

Samples having the compositions listed in the following Tables 3 and 4 were each prepared and evaluated for the above-mentioned respective items.

TABLE 3

|  | Comparative Example 12 | Example 2 | Example 3 | Example 4 | Example 5 |
|---|---|---|---|---|---|
| Dimethyldistearylammonium hectorite | 2 | 2 | 2 | 2 | 2 |
| PEG-9 polydimethylsiloxyethyl dimethicone | 1 | 1 | 1 | 1 | 1 |
| Polyethylene glycol diisostearate (PEG-3) | 0.5 | — | — | — | — |
| Polyethylene glycol diisostearate (PEG-4) | — | 0.5 | — | — | — |
| Polyethylene glycol diisostearate (PEG-8) | — | — | 0.5 | — | — |
| Polyethylene glycol diisostearate (PEG-12) | — | — | — | 0.5 | — |
| Polyethylene glycol isostearate (PEG-10) | — | — | — | — | 0.5 |
| Methylpolysiloxane 6cs (non-volatile silicone oil) | 5 | 5 | 5 | 5 | 5 |
| Methylphenylpolysiloxane (non-volatile silicone oil) | 4 | 4 | 4 | 4 | 4 |
| Isohexadecane (volatile hydrocarbon oil) | 7 | 7 | 7 | 7 | 7 |
| Isododecane (volatile hydrocarbon oil) | 10 | 10 | 10 | 10 | 10 |
| Trisodium edetate | 0.05 | 0.05 | 0.05 | 0.05 | 0.05 |
| Citric acid | 0.05 | 0.05 | 0.05 | 0.05 | 0.05 |
| Sodium citrate | 0.05 | 0.05 | 0.05 | 0.05 | 0.05 |
| Glycerin | 17 | 17 | 17 | 17 | 17 |
| Dietary salt | 0.5 | 0.5 | 0.5 | 0.5 | 0.5 |
| Phenoxyethanol | 0.5 | 0.5 | 0.5 | 0.5 | 0.5 |
| Purified water | Balance | Balance | Balance | Balance | Balance |
| Oil gel state | X | ○ | ○ | ○ | ○ |
| Emulsification property | ○ | ○ | ○ | ○ | ○ |
| Stability over time 4 weeks | Fine | Fine | Fine | Fine | Fine |
| Usability | X | Fine | Fine | Fine | Fine |

TABLE 4

|  | Example 6 | Example 7 | Example 8 | Example 9 |
|---|---|---|---|---|
| Dimethyldistearylammonium hectorite | 1.5 | 3 | 2 | 2 |
| PEG-9 polydimethylsiloxyethyl dimethicone | 1 | 1 | 1 | 1 |
| Polyethylene glycol diisostearate (PEG-3) | — | — | — | — |
| Polyethylene glycol diisostearate (PEG-4) | — | — | — | — |
| Polyethylene glycol diisostearate (PEG-8) | 0.5 | 0.5 | 0.5 | 0.5 |
| Polyethylene glycol diisostearate (PEG-12) | — | — | — | — |
| Polyethylene glycol isostearate (PEG-10) | — | — | — | — |
| Methylpolysiloxane 6cs (non-volatile silicone oil) | 5 | 5 | 5 | 5 |
| Methylphenylpolysiloxane (non-volatile silicone oil) | 4 | 4 | 4 | 4 |
| Isohexadecane (volatile hydrocarbon oil) | 7 | 7 | 20 | — |
| Isododecane (volatile hydrocarbon oil) | 10 | 10 | — | 20 |
| Trisodium edetate | 0.05 | 0.05 | 0.05 | 0.05 |
| Citric acid | 0.05 | 0.05 | 0.05 | 0.05 |
| Sodium citrate | 0.05 | 0.05 | 0.05 | 0.05 |
| Glycerin | 17 | 17 | 17 | 17 |

TABLE 4-continued

|  | Example 6 | Example 7 | Example 8 | Example 9 |
|---|---|---|---|---|
| Dietary salt | 0.5 | 0.5 | 0.5 | 0.5 |
| Phenoxyethanol | 0.5 | 0.5 | 0.5 | 0.5 |
| Purified water | Balance | Balance | Balance | Balance |
| Oil gel state | ○ | ○ | ○ | ○ |
| Emulsification property | ○ | ○ | ○ | ○ |
| Stability over time 4 weeks | Fine | Fine | Fine | Fine |
| Usability | Fine | Fine | Fine | Fine |

In Comparative Example 12 that contained a polyethylene glycol diisostearate comprising only three oxyethylene groups, a homogeneous oil gel was not obtained, and the feeling of use was oily. On the other hand, Examples 2 to 9 that contained a polyethylene glycol diisostearate comprising 4 to 12 oxyethylene groups were excellent in both emulsification stability and usability.

Formulation Example 1

Skin Cream

| Incorporated components Incorporation amounts | (% by mass) |
|---|---|
| (1) Liquid paraffin | 5 |
| (2) Isohexadecane | 7 |
| (3) Methylpolysiloxane 6cs | 12 |
| (4) Isododecane | 3 |
| (5) Cetyl 2-ethylhexanoate | 5 |
| (6) Polyethylene glycol diisostearate PEG8 | 0.5 |
| (7) PEG-9 polydimethylsiloxyethyl dimethicone | 1.5 |
| (8) Dimethyldistearylammonium hectorite | 2 |
| (9) Glycerin | 9 |
| (10) 1,3-Butyleneglycol | 7 |
| (11) Sorbit liquid | 2 |
| (12) Polyethylene glycol 6000 | 1 |
| (13) Tranexamic acid | 2 |
| (14) Polyvinyl alcohol | 0.5 |
| (15) Trisodium edetate | 0.1 |
| (16) Citric acid | 0.08 |
| (17) Sodium citrate | 0.02 |
| (18) Phenoxyethanol | suitable amount |
| (19) Purified water | balance |

Production method: (1) to (8) were dispersed homogeneously at room temperature (oil phase). On the other hand, (9) to (19) were dissolved by mixing homogeneously at room temperature (aqueous phase). The aqueous phase was added to the oil phase and emulsified in a homomixer to give an intended skin cream.

Formulation Example 2

Skin Cream

| Incorporated components Incorporation amounts | (% by mass) |
|---|---|
| (1) Isododecane | 14 |
| (2) Isohexadecane | 7 |
| (3) Methylpolysiloxane 6cs | 9 |
| (4) Octylmethoxy cinnamate | 1 |
| (5) Polyethylene glycol diisostearate PEG8 | 0.5 |
| (6) PEG-9 polydimethylsiloxyethyl dimethicone | 1 |
| (7) Dimethyldistearylammonium hectorite | 2 |
| (8) Titanium oxide | 2 |
| (9) Glycerin | 5 |
| (10) 1,3-Butylene glycol | 5 |
| (11) Dipropylene glycol | 5 |
| (12) Polyethylene glycol 20000 | 2 |
| (13) Potassium 4-methoxysalicylic acid | 1 |
| (14) Trisodium editate | 0.1 |
| (15) Citric acid | 0.1 |
| (16) Sodium citrate | 0.1 |
| (17) Dietary salt | 1 |
| (18) Phenoxyethanol | suitable amount |
| (19) Purified water | balance |

Production method: (1) to (6) were dispersed homogeneously at room temperature (oil phase). On the other hand, (7) to (19) were dissolved by mixing homogeneously at room temperature (aqueous phase). The aqueous phase was added to the oil phase and emulsified in a homomixer to give an intended skin cream.

Skin Cream

| Incorporated components Incorporation amounts | (% by mass) |
|---|---|
| (1) Isododecane | 25 |
| (2) Isohexadecane | 10 |
| (3) Methylpolysiloxane 6cs | 2 |
| (4) Vaseline | 1 |
| (5) Polyethylene glycol diisostearate PEG8 | 0.5 |
| (6) PEG-9 polydimethylsiloxyethyl dimethicone | 1.5 |
| (7) Dimethyldistearylammonium hectorite | 2 |
| (8) Dextrin palmitate | 1 |
| (9) Glycerin | 2 |
| (10) 1,3-Butylene glycol | 3 |
| (11) Dipropylene glycol | 2 |
| (12) Marine collagen | 0.1 |
| (13) Trisodium editate | 0.1 |
| (14) Citric acid | 0.05 |
| (15) Sodium citrate | 0.05 |
| (16) Dietary salt | 1 |
| (17) Phenoxyethanol | suitable amount |
| (18) Purified water | balance |

Production method: (1) to (8) were dispersed homogeneously at 70° C. (oil phase). On the other hand, (9) to (18) were dissolved by mixing homogeneously at room temperature (aqueous phase). The aqueous phase was added to the oil phase and emulsified in a homomixer to give an intended skin cream.

The invention claimed is:

1. A water-in-oil-type emulsion skin cosmetic comprising:
   (A) 3 to 25% by mass of a volatile hydrocarbon oil;
   (B) 0.1 to 15% by mass of a non-volatile silicone oil selected from the group consisting of methylpolysiloxane, methylphenylpolysiloxane, amino-modified silicone, and fluorine-modified dimethylpolysiloxane;
   (C) 0.1 to 0.8% by mass of a polyethylene glycol mono- or di-isostearate comprising 4 to 12 oxyethylene groups;

(D) 0.1 to 5% by mass of a polyoxyethylene-polydimethylsiloxyethyl-dimethicone copolymer; and (E) an organically-modified clay mineral.

2. The water-in-oil-type skin cosmetic according to claim 1, wherein the volatile hydrocarbon oil is one or a mixture of two or more of isododecane, isohexadecane and hydrogenated polyisobutene.

3. The water-in-oil-type skin cosmetic according to claim 1, wherein the polyoxyethylene-polydimethylsiloxyethyl-dimethicone copolymer is PEG-9 polydimethylsiloxyethyl dimethicone.

4. The water-in-oil-type skin cosmetic according to claim 1, wherein the organically-modified clay mineral is dimethyldistearylammonium hectorite.

5. The water-in-oil-type skin cosmetic according to claim 2, wherein the polyoxyethylene-polydimethylsiloxyethyl-dimethicone copolymer is PEG-9 polydimethylsiloxyethyl dimethicone.

6. The water-in-oil-type skin cosmetic according to claim 2, wherein the organically-modified clay mineral is dimethyldistearylammonium hectorite.

7. The water-in-oil-type skin cosmetic according to claim 3, wherein the organically-modified clay mineral is dimethyldistearylammonium hectorite.

* * * * *